US006033875A

United States Patent [19]

Bussineau et al.

[11] Patent Number: 6,033,875
[45] Date of Patent: *Mar. 7, 2000

[54] METHOD OF IMPROVED PRODUCTION OF INSULIN-LIKE GROWTH FACTOR

[75] Inventors: Christopher M. Bussineau, Hayward; Glenn Dorin, San Rafael; Robert D. Kudrna, Alameda, all of Calif.

[73] Assignee: Chiron Corporation, Emeryville, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/789,194

[22] Filed: Jan. 24, 1997

Related U.S. Application Data

[63] Continuation of application No. 08/302,594, Sep. 8, 1994, abandoned.

[51] Int. Cl.⁷ .................................................. C12N 15/18
[52] U.S. Cl. ........................ 435/69.4; 435/69.7; 435/69.9; 435/255.1; 435/255.2; 435/320.1; 435/325
[58] Field of Search .................... 435/69.1, 69.4, 435/325, 69.7, 320.1, 69.9, 172.3, 255.1, 255.2

[56] References Cited

U.S. PATENT DOCUMENTS

| | | | |
|---|---|---|---|
| 4,738,921 | 4/1988 | Belagaje et al. | 435/68.1 |
| 4,783,524 | 11/1988 | Larsen et al. | 530/350 |
| 4,810,646 | 3/1989 | Jamas et al. | 435/101 |
| 4,870,008 | 9/1989 | Brake | 435/70.1 |
| 4,876,242 | 10/1989 | Applebaum et al. | 514/3 |
| 4,963,665 | 10/1990 | Rotwein et al. | 536/23.5 |
| 4,992,540 | 2/1991 | Jamas et al. | 536/123 |
| 5,028,531 | 7/1991 | Ueda et al. | 435/69.4 |
| 5,158,875 | 10/1992 | Miller et al. | 435/69.1 |
| 5,210,028 | 5/1993 | Schmitz et al. | 435/69.4 |
| 5,231,178 | 7/1993 | Holtz et al. | 530/399 |
| 5,288,931 | 2/1994 | Chang et al. | |
| 5,324,639 | 6/1994 | Brierley et al. | 435/69.4 |
| 5,407,810 | 4/1995 | Builder et al. | |
| 5,410,026 | 4/1995 | Chang et al. | |
| 5,446,024 | 8/1995 | Builder et al. | 514/12 |
| 5,451,660 | 9/1995 | Builder et al. | |
| 5,612,198 | 3/1997 | Brierley et al. | |
| 5,650,496 | 7/1997 | Brierley et al. | |

FOREIGN PATENT DOCUMENTS

| | | |
|---|---|---|
| 123 228 | 10/1984 | European Pat. Off. . |
| 128 733 | 12/1984 | European Pat. Off. . |
| 135 094 | 3/1985 | European Pat. Off. . |
| 155 655 | 9/1985 | European Pat. Off. . |
| 206783 | 12/1986 | European Pat. Off. . |
| 219 814 | 4/1987 | European Pat. Off. . |
| 264 074 | 4/1988 | European Pat. Off. . |
| 0286345 A2 | 10/1988 | European Pat. Off. . |
| 303 855 | 2/1989 | European Pat. Off. . |
| 324 274 | 7/1989 | European Pat. Off. . |
| 379 338 | 7/1990 | European Pat. Off. . |
| 0409814 A1 | 1/1991 | European Pat. Off. . |
| 434 625 | 6/1991 | European Pat. Off. . |
| 436 469 | 7/1991 | European Pat. Off. . |
| 478 333 | 9/1991 | European Pat. Off. . |
| 501 914 | 9/1992 | European Pat. Off. . |
| 560 723 | 9/1993 | European Pat. Off. . |
| 561 137 | 9/1993 | European Pat. Off. . |
| 0 567 554 B1 | 11/1993 | European Pat. Off. . |
| 63-169733 | 7/1988 | Japan . |
| 63-196524 | 8/1988 | Japan . |
| 63-263085 | 10/1988 | Japan . |
| 63-269984 | 11/1988 | Japan . |
| 85/00831 | 2/1985 | WIPO . |
| 89/03423 | 4/1989 | WIPO . |
| 91/04282 | 4/1991 | WIPO . |
| 92/04363 | 3/1992 | WIPO . |
| WO 92/12993 | 8/1992 | WIPO . |
| 92/17594 | 10/1992 | WIPO . |
| 92/22653 | 12/1992 | WIPO . |
| 93/08826 | 5/1993 | WIPO . |
| 93/11240 | 6/1993 | WIPO . |
| WO 95/06059 | 3/1995 | WIPO . |
| WO 95/06064 | 3/1995 | WIPO . |
| WO 95/07978 | 3/1995 | WIPO . |
| WO 95/16701 | 6/1995 | WIPO . |
| WO 95/16777 | 6/1995 | WIPO . |
| WO 96/07744 | 3/1996 | WIPO . |

OTHER PUBLICATIONS

K. Axelsson et al., "Disulfide arragnement of human insulin–like growth factor I derived from yeast and plasma" *Eur. J. Biochem.* (1992) 206:987–994.

J.Y. Chang et al., "Single–Step Solubilization and Folding of IGF–1 Aggregates from *Escherichia coli*" Protein Folding: in vivo and in vitro (American Chemical Society, 1993) pp. 178–188.

S. Elliott et al., "Yeast–Derived Recombinant Human Insulin–Like Growth Factor I: Production, Purification, and Structural Characterization" *J. Protein Chem.* (1990) 9:95–104.

G. Forsberg et al., "Separation and characterization of modified variants of recombinant human insulin–like growth factor I derived from a fusion protein secreted from *Escherichia coli*" *Biochem. J.* (1990) 271:357–363.

R.A. Hart et al. "Effect of environment on insulin–like growth factor I refolding selectivity" *Biotechnol. Appl. Biochem.* (1994) 20:217–234.

K.R. Hejnaes et al., "Development of an optimized refolding process for recombinant Ala–Glu–IGF–I" *Prot. Eng.* (1992) 5:797–806.

S. Hober et al., "Disulfide Exchange Folding of Insulin–like Growth Factor I" *Biochem.* (1992) 31:1749–1756.

(List continued on next page.)

Primary Examiner—Marianne P. Allen
Attorney, Agent, or Firm—Roberta L. Robins; Joseph H. Guth; Robert P. Blackburn

[57] ABSTRACT

The present invention relates to a method of making a recombinant protein in high yields by adding alkali to a cell culture that is capable of producing recombinant protein. The recombinant protein can be any protein that is suitable to be made by recombinant techniques, such as IGF.

17 Claims, 1 Drawing Sheet

OTHER PUBLICATIONS

H. Meng et al., "Reduction Studies on Bacterial Recombinant Somatomedin C/Insulin–like Growth Factor" *J. Chromatog.* (1988) 443:183–192.

J.A. Miller et al., "Oxidative Refolding of Insulin–like Growth Factor I Yields Two Products of Similar Thermodynamic Stability: A Bifurcating Protein–Folding Pathway" *Biochemistry* (1993) 32:5203–5213.

L.O. Narhi et al., "role of Native Disulfide Bonds in the Structure and Activity of Insulin–like Growth Factor I: Genetic Models of Protein–Folding Intermediates" *Biochemistry* (1993) 32:5214–5221.

M. Niwa et al., "Chemical Synthesis, cloning, and Expression of Genes for Human Somatomedin C (Insulin–like Growth Factor I) and $^{59}$Val–Somatomedic C" *Ann. NY Acad. Sci.* (1986) 469:31–52.

E. Samuelsson et al. "Enhanced in Vitro Refolding of Insulin–like Growth Factor I using a Solubilizing Fusion Partner" *Biochemistry* (1994) 33:4207–4211.

Barr, *Bio/Technology*, (1987) 5:486.

Beier, *Nature*, (1982) 300:724.

Brake, *PNAS (USA)*, (1984) 81:4642.

Buergisser, *Biochem. Biophys. Res. Comm.* (1990) 169:832.

De Nobel, *J. of Gen. Microbiol.*, (1989) 135:2077.

Hampton, *J. of Biol. Chem.* (1989) 264:19155.

Hinnen, *PNAS (USA)*, (1978) 75:1929.

Huang, *Biotech. and Bioeng.* (1991) 38:977.

Rinderknecht, *J Biol Chem*, (1978) 253:2769.

Rinderknecht, *FEBS Letters*, (1978) 89:283.

Rogachefsky, *Osteoarthritis and Cartilage*, (1993) 1:105–114.

Urdea, *PNAS (USA)*, (1983) 80:7461.

Li, *PNAS*, (1983) 80:2216–2220.

Wells, *Gene*, (1985) 34:315.

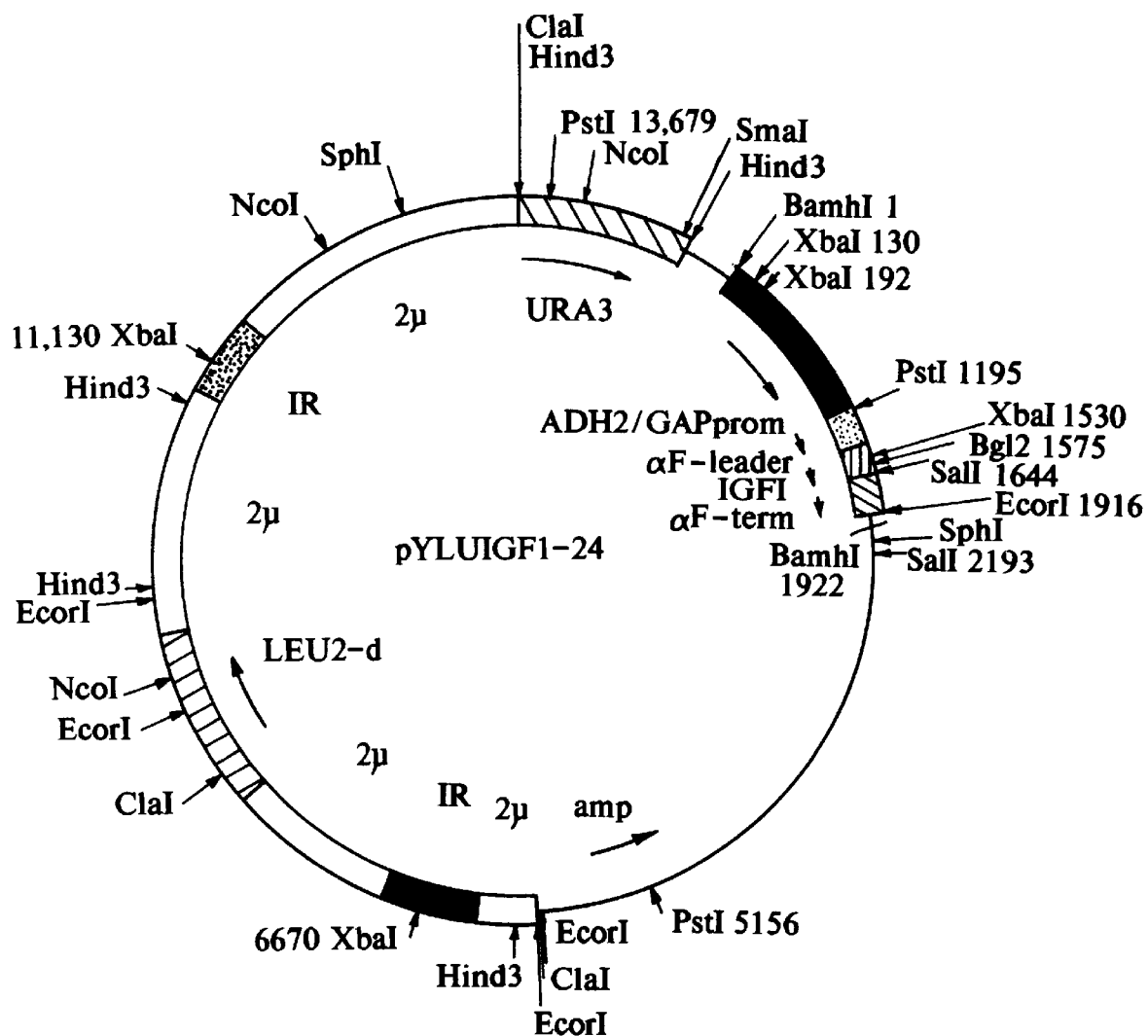

METHOD OF IMPROVED PRODUCTION OF INSULIN-LIKE GROWTH FACTOR

This application is a continuation of application Ser. No. 08/302,594 filed on Sep. 8, 1994, now abandoned.

BACKGROUND OF THE INVENTION

This invention relates to making insulin-like growth factor (IGF), including IGF-I and IGF-II, in high yield.

Insulin-like growth factors, each with a molecular weight of about 7,500 daltons, possess A and B domains that are highly homologous to the corresponding domains of proinsulin. The A and B domains are connected to each other by a C domain. A carboxy terminal extension, the D domain, is present in IGF but is not found in proinsulin. Both IGF-I and IGF-II are single-chain polypeptides each with 3 disulfide bridges and have a sequence identity of 49% and 47%, respectively, to human insulin A and B chains. Like insulin, IGF stimulate phosphorylation of specific tyrosine residues within the cytoplasmic domain of the receptors to which they bind, as described in WO 93/98826. The designation "insulin-like growth factor" was chosen to express the insulin-like effects and the insulin-like structure of these polypeptides which act as mitogens on a number of cells, as described in EP 128 733. IGF-I is a 70 amino acid peptide, while IGF-II is a 67 amino acid peptide, as described in Rinderknecht, *J Biol Chem*, (1978) 253:2769; and Rinderknecht, *FEBS Letters*, (1978) 89:283. IGF-I and IGF-II have 62% structural homology to each other. Both have been isolated from human serum.

Insulin-like growth factors are also known under the class name somatomedins, and have been identified in various animal species as polypeptides that act to stimulate growth of cells in a variety of tissues and cell types, particularly during development. Growth promoting effects of somatomedins include enhancement of cell multiplication and stimulation of cartilage proliferation, stimulation of transport of amino acids, synthesis of RNA, DNA and protein, and stimulation of incorporation of sulfate into proteoglycan and of proline into collagen. Much mammalian postnatal growth is due to stimulation of cartilage growth by somatomedins and growth in utero may also be somatomedin-dependent.

Uses of IGF as a known stimulatory and growth promoting agent includes use for bone repair and replacement therapy, as described in EP 303 855; as a means to counteract certain harmful side effects of carcinostatic drugs, as described in JP 63-196524; and as a way to increase lactation and meat production in cattle and other farm animals, as described in U.S. Pat. No. 4,783,524.

IGF-I has also been found useful in the treatment of osteoporosis in mammals exhibiting decreased cortical bone mineral density and those exposed to drugs or environmental conditions that result in bone density reduction and potentially to an osteoporosis condition, as described in EP 560 723 and EP 436 469.

IGF-I has been administered with sodium pentosan polysulfate (PPS) to severely osteoarthritic canines with the effect of reducing the severity of the disease by lowering the levels of active neutral metalloproteinase in the cartilage. In the model of mildly osteoarthritic canines, therapeutic intervention with IGF-I and PPS together appeared to successfully maintain cartilage structure and biochemistry, while IGF alone was ineffective, as described in Rogachefsky, *Osteoarthritis and Cartilage*, (1993) 1:105–114. Recombinant proteins have been made by many processes known in the art, as described in U.S. Pat. No. 4,870,008, EP 324 274, EP 123 228, EP 501 914, EP 128 733, WO 93/11240, EP 135 094, U.S. Pat. No. 5,158,875, WO 85/00831, EP 264 074, EP 219 814, EP 155 655, EP 379 338, U.S. Pat. No. 4,876,242, U.S. Ser. No. 578,728, U.S. Ser. No. 747,152, U.S. Pat. No. 4,963,665, U.S. Ser. No. 681,688, U.S. Ser. No. 837,313, WO 89/03423, U.S. Pat. No. 5,210,028, and U.S. Pat. No. 5,231,178.

Moreover, IGF can be produced in methylotrophic yeast transformants with the IGF coding sequence linked to a signal sequence which direct secretion and proteolytic processing of the protein product. The signal sequence suitable herein includes the *S. cerevisiae* alpha mating factor pre-pro sequence in protease deficient *P. pastoris* strains, as described in WO 92/04363.

Recombinant IGF can be grown and harvested in favorable growth conditions as described in U.S. Pat. No. 4,810,646 and U.S. Pat. No. 4,992,540.

IGF-I and IGF-II have been expressed and secreted using a leader sequence that contains a portion of the yeast α-factor signal sequence, as described in EP 128 733.

It would be advantageous to produce IGF in high yield using a Saccharomyces host cell.

SUMMARY OF THE INVENTION

It is an object of the present invention to discover and provide for an improved method of producing IGF in high yield.

It is another object of the invention to provide an improved method of producing IGF using a host cell that is selected for high yield of IGF.

It is a further object of the invention to provide a method of producing IGF in high yield where the IGF-producing cell is cultured under conditions that are selected for high yield of IGF, such as selected growth media, selected temperature, and selected pH.

It is yet another object of the invention to add an alkali to the cell culture at the end of the fermentation period to improve yield of IGF produced by the cell.

BRIEF DESCRIPTION OF THE DRAWINGS

FIG. 1 shows plasmid map of rhIGF expression plasmid pYLUIGF1–24.

DETAILED DESCRIPTION OF THE PREFERRED EMBODIMENTS

The inventors herein have discovered a method of making recombinant proteins in high yield in yeast cells by introducing an alkaline shock treatment when yeast cells containing DNA encoding the recombinant protein are cultured in a fermentation medium for induction of production of the recombinant protein. Such alkaline shock treatment is introduced at the end of the fermentation period. The invention is exemplified herein by the expression and production of IGF. However, the invention is applicable to the production of any other recombinant protein that can be produced by yeast, such as PDGF, EGF, FGF, and the like.

The term "insulin-like growth factor" or IGF as used herein encompasses IGF-I and IGF-II and includes biologically active fragments, analogues, muteins, including C-terminal deletion muteins, and derivatives thereof that retain IGF activity and/or ability to bind the IGF receptors, as described in, for example, EP 135 094, WO 85/00831, U.S. Pat. No. 4,738,921, WO 92/04363, U.S. Pat. No. 5,158,875, EP 123 228, and EP 128 733.

An analog of IGF or an analog of the fragment includes native IGF that has been modified by one or more amino acid insertion, deletion, or substitution that does not substantially affect its properties. Preferably, the analog has increased activity compared to native IGF. More preferably, at least 2-fold increase, most preferably, at least 7–10 fold increase. For example, the analog can include conservative amino acid substitutions. An IGF analog also includes peptides having one or more peptide mimics ("peptoids"), such as those described in WO 91/04282.

An IGF mutein is polypeptide variant with one or more amino acids altered to produce a desired characteristic such as to eliminate a cysteine residue. Muteins, analogues and derivatives may be generated using conventional techniques. For example, PCR mutagenesis can be used. While the following discussion refers to DNA, it is understood that the technique also finds application with RNA. An example of a PCR technique is described in WO 92/22653. Another method for making analogs, muteins, and derivatives, is cassette mutagenesis based on the technique described by Wells, *Gene*, (1985) 34:315.

The method for obtaining recombinant proteins in high yield that is suitable herein can be substantially as described in U.S. Pat. No. 4,810,646, issued Mar. 7, 1989 and U.S. Pat. No. 4,992,540, issued Feb. 12, 1991. The alkaline shock treatment involves addition of an alkali, such as hydroxides of alkali metals and alkaline earth metals, or other suitable hydroxides that is not detrimental to the yield of the recombinant protein. An amount of the alkali is added herein sufficient to adjust the final pH of the culture medium to one in a range of between about pH 8–9, preferably, about pH 9–10, more preferably pH 10–11. Alternatively, the pH can be in a range of pH 11–12. In a preferred embodiment of the present invention, the pH of the medium during alkaline shock treatment is about pH 9.5, preferably pH 10.5. Alternatively, a preferred pH can be pH 11.5.

The cells herein are exposed to the alkaline shock for a period ranging from about 30 minutes to about 10 hours, preferably, about 30 minutes to about 2 hours, or about 30 minutes to about 4 hours, or about 30 minutes to about 6 hours, or about 30 minutes to about 8 hours. More preferably, the alkaline shock treatment lasts about 1–3 hours, or about 1–5 hours, or about 1–7 hours, or about 1–9 hours. Most preferably, the alkaline shock treatment lasts for about 2–4 hours, or about 3–4 hours, or about 4–5 hours, or about 5–6 hours, or about 6–7 hours, or about 7–8 hours, or about 8–9 hours, or about 9–10 hours, or overnight.

In another preferred embodiment of the present invention, an amount of thiol can be added to the fermentation medium. This thiol can be added also at the end of the fermentation period. Preferably, the thiol is added before the alkaline shock treatment. The amount of thiol to be added can be one within the range of between about 0.05 mM to about 50 mM, or between about 0.2 mM and about 2 mM, or between about 0.05 mM and about 1 mM, or between about 0.5 mM and about 20 mM, or between about 2 mM and about 10 mM, or between about 3 mM and about 15 mM.

In an embodiment of this invention, the yield of the recombinant protein can be improved by maintaining the host cells at a selected temperature during the alkaline shock treatment. In a preferred embodiment of the present invention, the culture temperature is in a range of about 5° C. to about 10° C., about 10° C. to about 20°, about 15° C. to about 25° C., about 20° C. to about 30° C., about 25° C. to about 30° C., or about 25° C. to about 35° C., or about 25° C. to about 40° C., or about 25° C. to about 45° C., or about 30° C. to about 35° C., or about 35° C. to about 40° C., or about 40° C. to about 45° C., or about 45° C. to about 50° C. Preferably, the temperature is between about 25° C. to about 35° C.

Yield of the recombinant protein can be increased further, in addition to alkaline shock treatment, by addition of DTT or use of other chaotropic agents and/or detergent with enzymes, as described in WO 93/11240, De Nobel, *J. of Gen. Microbiol.*, (1989) 135:2077, and Huang, *Biotech. and Bioeng.* (1991) 38:977.

The following example is illustrative of a preferred method of making IGF.

EXAMPLE I

The rhIGF-I protein was synthesized by *Saccharomyces cerevisiae* strain JSC417, transformed with plasmid pYLUIGF1–24. The yeast strain JSC417, was deposited with the American Type Culture Collection (ATCC) located at 12301 Parklawn Drive, Rockville, Md. 20852, on Aug. 2, 1994 with ATCC Accession No. 74295. Strain JSC417 was derived from strain AB110. JSC417 has the following genotype: Matα, ura 3–52, leu 2, pep 4-3, his 4–580, [cir °].

Expression of rhIGF-I in *S. cerevisiae* strain JSC417 was non-constitutive and under the regulation of a hybrid ADH2-GAP promoter derived from promoter sequences of the yeast alcohol dehydrogenase as described in Beier, *Nature*, (1982) 300:724, and glyceraldehyde-3-phosphate dehydrogenase as described in EP 120 551. In addition, the rhIGF-I sequences are fused to the yeast α-factor leader which allows for secretion, and to the yeast α-factor terminator both as described in Brake, *PNAS (USA)*, (1984) 81:4642. Induction of rhIGF-I expression is achieved by maintaining low concentration of glucose in the growth medium during fermentation.

Plasmid pYLUIGF1–24 is a yeast expression vector which contains the sequence coding for rhIGF-I cloned into the BamHI site of vector pAB24, as described in Barr, *Bio/Technology*, (1987) 5:486, as well as pBR322 sequences including the ampicillin resistant (ampR) gene, 2-micron (2μ) sequences, and the yeast LEU 2 and URA 3 genes. The expression cassette for rhIGF-I consisted of (5' to 3') ADH2 regulatory sequences, a GAP promoter, α-factor leader, rhIGF-I synthetic gene and α-factor terminator, as described in EP 123 228.

The rhIGF-I gene cloned into the expression cassette was chemically synthesized using the phosphoramidite procedure as described by Urdea, *PNAS (USA)*, (1983) 80:7461, and according to the Dayhoff amino acid sequences.

*S. cerevisiae* cells were transformed with plasmid pYLUIGF1–24 following a standard protocol as described in Hinnen, *PNAS (USA)*, (1978) 75:1929. Briefly, the transformation mixture was plated onto uracil-deficient selective plates that were yeast nitrogen base with amino acids containing 2% glucose and incubated for four days at 30° C. Transformant colonies were transferred into leucine-deficient, selective media with 8% glucose, and grown at 30° C. Expression of rhIGF-I was accomplished by growing the yeast transformants in uracil-deficient medium with 4% glucose at 30° C. for 48 hours. Expression of rhIGF-I in the medium at 48 hours was analyzed by any of several standard methods including RP-HPLC, SDS-PAGE, RIA, or radioreceptor assay.

Production of rhIGF-I involves successive amplification of the yeast cells contained within the seedstock aliquot. The first amplification stage was carried out in shake flasks at a controlled temperature of about 30° C. in a rotary shakerincubator. Approximately $10^7$ cells were thawed into about 500 mL of uracil- and leucine-deficient media, as described above, containing 5–8% glucose. After about 25–45 hours, preferably about 35±2 hours, the flask contents were transferred to a small fermentation vessel for the second stage of cell amplification. This culture was grown for about 24±4 hours under controlled temperature within a range of about 25° C. to about less than 40° C., about 25°–30° C., about 25°–35° C., about 25°–45° C., about 30°–35° C., about 30°–40° C., or about 35°–40° C., with aeration (1 vvm) and agitation (400–600 rpm) in 10 L of the same media used for stage I. 10–30 L of the stage II culture was transferred to a larger, production-scale fermentation vessel (10,000 L) for the final amplification and rhIGF-I expression phase of growth. Stage III utilized a semi-defined growth media containing casein hydrolyzate, basal salts, vitamins, trace elements, and antifoam. The casein hydrolyzate employed may be any commercial brand with a composition of at least 5% amino-nitrogen, at least 10% total nitrogen, not more than 20% ash, but preferably would have a composition comparable to that of N-Z-Amine HD (Quest). The antifoam employed may be any of several commercially available polyalcohol- or silicon-based compounds. The media is listed in Tables 1 and 2 below. The fermentation was carried out at constant 30° C., pH 6 (by addition of 50% sodium hydroxide or 75% phosphoric acid), aeration (0.8 vvm), pressure (5–12 psig), and glucose feed rate with constant agitation. The fermentation is known to those skilled in the art as a fed-batch mode of operation, so-called because the fermentor is initially filled to less than capacity (for example approximately 50%), allowing for the addition of a suitable amount of a glucose feed solution with a concentration of about 25–50% (w/v). For a media composition described as low range in Tables 1 and 2, for example, 800–900 kg glucose is added to the fermentor over the duration of the run at a rate of addition that depends on yeast cell density and residual glucose concentration. Typically, glucose is added at about 500 g/min for approximately the first 26 h, at about 1000 g/min for approximately the next 24 h, and finally at about 500 g/min until completion. Cell growth concomitant with product expression occurs once the media becomes depleted of excess glucose, and may continue until the culture reaches the desired cell density of approximately 35 gDCW/L. If the media composition is greater than that given in the low range of Tables 1 and 2, the rate of addition of glucose, for example, may be increased to about 1500 g/min after the first 24 hours of fermentation.

Thiols reducing agents including, for example dithiothreitol, cysteine, glutathione, β-mercaptoethanol, monothioglycerol, and mercaptoacetic acid, were added prior to pH shock to increase the yield of monomeric IGF. Addition of a chaotropic agent including, for example, urea, further increases the yield of monomer. The thiols were added in a concentration range from between about 0.05–50 mM, between about 0.2–2 mM, between about 0.05–1 mM, between about 0.5–20 mM, between about 2–10 mM, and between about 3–15 mM.

rhIGF-I can be recovered from the cell cultures using conventional techniques. At the completion of fermentation, prior to cell removal, the pH of the fermentor culture can be raised to a pH in the range of about pH 9–10, about pH 10.1–10.3, about pH 10.4–10.6, about pH 10.6–10.8, about pH 10.9–10.11, or about pH 11–12 for about 30 minutes. About 50% sodium hydroxide is added to the fermentor to raise the pH of the whole culture to with a range of about pH 9–10, about pH 10.1–10.3, about pH 10.4–10.6, about pH 10.6–10.8, about pH 10.9–10.11, or about pH 11–12 for a second time period in a range of about 30 minutes to 10 hours, about 30 minutes to 8 hours, about 30 minutes to 6 hours, about 30 minutes to 4 hours, about 30 minutes to 2 hours, about 1–10 hours, about 1–8 hours, about 1–6 hours, about 1–4 hours, about 1–2 hours, about 2–10 hours, about 2–8 hours, about 2–6 hours, about 2–4 hours, about 2–3 hours, about 3–4 hours, about 4–5 hours, about 5–6 hours, about 6–7 hours, about 7–8 hours, about 8–9 hours, and about 9–10 hours. Afterwards the whole yeast were separated from the product-containing spent media by continuous centrifugation. After collection the supernatant was readjusted to with a range of about pH 3–4, about pH 5–6 or about pH 6–7 with about 75% phosphoric acid, and filtered using microporous tangential flow filtration prior to adsorbing on a cation exchange resin. The column was washed with 20 mM acetic acid and 100 mM potassium borate/0.1 mM EDTA buffers, and eluted with a 100 mM potassium borate/0.1 mM EDTA/300 mM potassium chloride buffer at pH 8.7.

Hydrophobic interaction chromatography (HIC) was used for primary purification of rhIGF-I. Ammonium sulfate precipitation and microporous tangential flow filtration was used to remove yeast contaminants. After washing the precipitate with ammonium sulfate, sodium acetate and EDTA buffer at pH 4, the material was loaded onto the HIC matrix and eluted with linear decreasing gradient of 0.9 to 0.5 M ammonium sulfate. Eluted protein at pH 4 was concentrated 20-fold and the buffer was exchanged using a 5000 MWCO tangential flow ultrafiltration membrane. The diafiltration agents employed were high purity water followed by 20 mM acetic acid.

Standard reverse-phase high performance liquid chromatography (RP-HPLC) was used to remove product-related species from the authentic rhIGF-I. The 5 K concentrate was loaded onto a suitable C8 matrix and eluted with a linear increasing gradient of 10% to 50% acetonitrile in a pH 6.8 ammonium acetate buffer.

TABLE 1

| Ingredients | Amount (g/10 L Final Volume) Low Range | Intermediate Low Range 2 × g/10 L | Intermediate High Range 3 × g/10 L | High Range 4.5 × g/10 L |
|---|---|---|---|---|
| CAA (casein hydrosylate) | 260.00 | 520.00 | 780.00 | 1170.00 |
| Glucose | 875.00 | 1750.00 | 2625.00 | 3937.50 |
| $NH_4SO_4$ | 50.00 | 100.00 | 150.00 | 225.00 |
| $KH_2PO_4$ | 10.00 | 20.00 | 30.00 | 45.00 |
| $MgSO_4 \cdot 7H_2O$ | 5.00 | 10.00 | 15.00 | 22.50 |
| NaCl | 1.00 | 2.00 | 3.00 | 4.50 |
| $CaCl_2 \cdot 2H_2O$ | 1.00 | 2.00 | 3.00 | 4.50 |

TABLE 2

| Ingredients | mg Low Range | Intermediate Low Range 2 × mg | Intermediate High Range 3 × mg | High Range 4.5 × mg |
|---|---|---|---|---|
| Na—$Mo \cdot 2H_2O$ | 0.82 | 1.64 | 2.46 | 3.69 |
| $H_3BO_3$ | 2.05 | 4.10 | 6.15 | 9.225 |
| $CuSO_4 \cdot 5H_2O$ | 0.16 | 0.32 | 0.48 | 0.72 |
| KI | 0.41 | 0.82 | 1.23 | 1.845 |
| $FeCl_3 \cdot H_2O$ | 0.82 | 1.64 | 2.46 | 3.69 |
| $MnSO_4 \cdot H_2O$ | 1.64 | 3.28 | 4.92 | 7.38 |
| $ZnSO_4$ | 1.64 | 3.28 | 4.92 | 7.38 |
| pantothenate | 323.00 | 646.00 | 969.00 | 1453.50 |
| myo-inositol | 323.00 | 646.00 | 969.00 | 1453.50 |
| thiamine | 23.20 | 46.40 | 69.60 | 104.40 |

TABLE 2-continued

| Ingredients | mg Low Range | Intermediate Low Range 2 × mg | Intermediate High Range 3 × mg | High Range 4.5 × mg |
|---|---|---|---|---|
| pyridoxine | 23.20 | 46.40 | 69.60 | 104.40 |
| biotin | 1.55 | 3.10 | 4.65 | 6.975 |
| PABA | 15.46 | 30.92 | 46.38 | 69.57 |
| riboflavin | 15.46 | 30.92 | 46.38 | 69.57 |
| folic acid | 1.55 | 3.10 | 4.65 | 6.975 |
| niacin | 23.20 | 46.40 | 69.60 | 104.40 |

The patents, patent applications and publications cited herein are incorporated by reference.

What is claimed:

1. A method for improved isolation of a recombinant, authentic, monomeric IGF-1 protein from a yeast cell culture medium into which IGF-1 protein has been secreted, the method comprising:

a) providing a yeast host cell that comprises a first DNA fragment that encodes the IGF-1 protein, a second DNA fragment that comprises a regulatory sequence for transcription and translation of the first DNA fragment, and a third DNA fragment that encodes a yeast secretory signal for secretion of the recombinant protein, wherein the first, second, and third DNA fragments are operatively linked to allow expression and secretion of the recombinant protein;

b) culturing the host cell for a first time period under conditions that result in production and secretion of the IGF-1 protein into the cell culture medium, wherein the conditions comprise an appropriate temperature and an appropriate pH;

c) adding an amount of an alkali solution to the cell culture medium sufficient to adjust the pH of the culture to a pH in a range of about pH 8–pH 12 and which results in the formation of authentic, monomeric IGF-1, upon termination of the first time period, wherein the alkali solution consists of an hydroxide of an alkali metal or an hydroxide of an alkaline earth metal; and d) recovering the recombinant, authentic, monomeric IGF-1 protein from the cell culture medium.

2. The method of claim 1, wherein the amount of the alkali is sufficient to adjust the pH of the culture to a pH in a range selected from the group consisting of about pH 8–9, about pH 9–10, about pH 10–11, and about pH 11–12.

3. The method of claim 2, wherein the pH is in the range of about pH 9–10.

4. The method of claim 2, wherein the pH is in the range of about pH 10–11.

5. The method of claim 2, wherein the pH is in the range of about pH 11–12.

6. The method of claim 1, wherein the host cell is exposed to the alkali for a second time period, wherein the second time period is in a range selected from the group consisting of: about 30 minutes to 10 hours, about 30 minutes to 8 hours, about 30 minutes to 6 hours, about 30 minutes to 4 hours, about 30 minutes to 2 hours, about 1–10 hours, about 1–8 hours, about 1–6 hours, about 1–4 hours, about 1–2 hours, about 2–10 hours, about 2–8 hours, about 2–6 hours, about 2–4 hours, about 2–3 hours, about 3–4 hours, about 4–5 hours, about 5–6 hours, about 6–7 hours, about 7–8 hours, about 8–9 hours, and about 9–10 hours.

7. The method of claim 6, wherein the alkali is sufficient to adjust the pH of the culture to a pH in a range selected from the group consisting of about pH 8–9, about pH 9–10, about pH 10–11, and about pH 11–12.

8. The method of claim 7, wherein the pH is in the range of about pH 9–10.

9. The method of claim 8, wherein the pH is about pH 9.5.

10. The method of claim 7, wherein the pH is in the range of about pH 10–11.

11. The method of claim 10, wherein the pH is about pH 10.5.

12. The method of claim 7, wherein the pH is in the range of about pH 11–12.

13. The method of claim 12, wherein the pH is about pH 11.5.

14. The method of claim 1, wherein the alkali is added to the cell culture at a temperature in a range selected from the group consisting of about 10° C. to 20° C., about 20° C. to 30° C., about 30° C. to 40° C., about 40° C. to 50° C., about 15° C. to 25°, about 25° C. to 35° C., and about 35° C. to 45° C.

15. The method of claim 1, wherein the amount of alkali solution is sufficient to adjust the pH of the culture to a pH in the range of about pH 10.4–10.6.

16. The method of claim 1, wherein the yeast host cell is *Saccharomyces cerevisiae*.

17. The method of claim 16, wherein the secretory signal is from *Saccharomyces cerevisiae*.

* * * * *